United States Patent
Nissilä

(10) Patent No.: US 6,754,517 B2
(45) Date of Patent: Jun. 22, 2004

(54) APPARATUS FOR MEASURING AN ELECTROCARDIOGRAPH SIGNAL

(75) Inventor: Seppo Nissilä, Oulu (FI)

(73) Assignee: Polar Electro Oy, Kempele (FI)

( * ) Notice: Subject to any disclaimer, the term of this patent is extended or adjusted under 35 U.S.C. 154(b) by 244 days.

(21) Appl. No.: 09/938,476

(22) Filed: Aug. 24, 2001

(65) Prior Publication Data

US 2002/0026114 A1 Feb. 28, 2002

(30) Foreign Application Priority Data

Aug. 30, 2000 (FI) .............................................. 20001914

(51) Int. Cl.$^7$ ............................................ A61B 5/0408
(52) U.S. Cl. ........................ 600/384; 600/393; 600/509
(58) Field of Search ................................ 600/384, 372, 600/382, 386, 393, 509, 547, 390

(56) References Cited

U.S. PATENT DOCUMENTS

| | | | |
|---|---|---|---|
| 4,120,294 A | 10/1978 | Wolfe | |
| 4,248,244 A | * 2/1981 | Charnitski et al. | ........... 600/519 |
| 5,203,330 A | * 4/1993 | Schaefer et al. | ............ 600/384 |
| 5,226,425 A | 7/1993 | Righter | |
| 5,289,824 A | * 3/1994 | Mills et al. | .................. 600/508 |
| 5,511,546 A | * 4/1996 | Hon | ............................ 600/490 |
| 6,018,677 A | 1/2000 | Vidrine et al. | |
| 6,114,832 A | * 9/2000 | Lappi et al. | ................. 320/108 |
| 6,149,602 A | * 11/2000 | Arcelus | ....................... 600/523 |

FOREIGN PATENT DOCUMENTS

| | | |
|---|---|---|
| EP | 0 444 934 A1 | 9/1991 |
| EP | 0 540 154 A1 | 5/1993 |
| GB | 2339833 A | 2/2000 |
| JP | 10314134 | 12/1998 |

OTHER PUBLICATIONS

Guyton, Arthur C., *Human Physiology and Mechanisms of Disease*, W.B. Saunders Company (1982) Chapter 13, pp. 128–133.

* cited by examiner

Primary Examiner—Kennedy Schaetzle
(74) Attorney, Agent, or Firm—Hoffmann & Baron, LLP

(57) ABSTRACT

An electrode structure for measuring an ECG signal on a person's skin. The electrode structure (100) to be arranged on the person's finger (102) comprises an inner surface (116) residing against the finger (102), which inner surface (116) of the electrode structure (100) comprises an inner surface electrode (118), the electrode structure (100) further comprising an outer surface (120) opposite to the inner surface (116), which outer surface (120) of the electrode structure (100) comprises an outer surface electrode (122) to be arranged against a point on the person's skin other than said finger (102) having the electrode structure (100) arranged thereon, the electrode structure being arranged to measure a potential difference caused by the ECG signal between a first electrode and a second electrode.

18 Claims, 4 Drawing Sheets

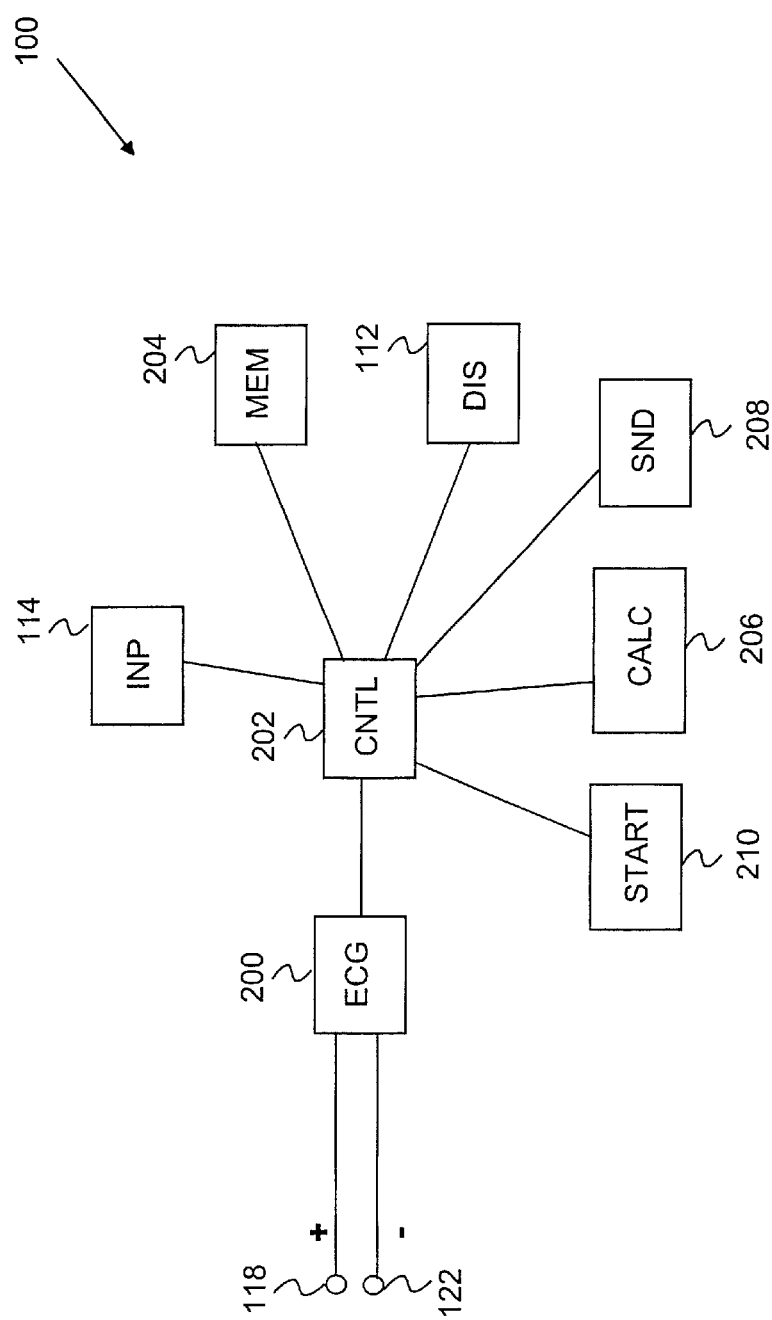

APPARATUS FOR MEASURING AN ELECTROCARDIOGRAPH SIGNAL

FIELD OF THE INVENTION

The invention relates to a device for measuring heart rate information non-invasively, particularly to a heart rate monitor used in connection with physical exercise and sports.

BRIEF DESCRIPTION OF THE RELATED ART

In connection with physical exercise, measurement of heartbeat rate presents an attractive task. The heartbeat rate, i.e. heart rate, provides information e.g. on a person's exercise intensity, recovery and changes in the physical condition, enabling the relationship between exercise and rest to be monitored and planned in a better way.

Heart rate is measured from a person's skin on the basis of an electrocardiographic (ECG) signal produced by a heartbeat. Further information on ECG can be found in *Human Physiology and Mechanisms of Disease* by Guyton, Arthur C., Third Edition, Chapter 13: The Electrocardiogram, W. B. Saunders Company 1982, ISBN 4-7557-0072-8, which is incorporated herein by reference. An electrocardiographic signal is an electromagnetic signal produced by the heartbeat, detected on the body of a person to be measured. The signal is measured using electrodes that at least at two points come into contact with the body. In practice, an electrode nearest to the heart on a polarization vector usually operates as the actual measuring electrode while another electrode provides ground potential, a voltage measured by the measuring electrode being compared to the ground potential as a function of time. Publication U.S. Pat. No. 6,018,677, which is incorporated herein by reference, discloses a method and apparatus for measuring heart rate on the basis of a measured ECG signal. FIG. 3A in patent application GB 2 339 833A filed by the present applicant discloses a prior art solution for positioning electrodes in a electrode belt. According to what has been disclosed in the publication, the electrode belt is placed on the chest while electrodes to be arranged against the chest measure the ECG signal produced by the heartbeat.

As far as user-friendliness is concerned, the prior art solution for measuring heart rate using an electrode belt is not an optimal arrangement for the user. The belt, which is of considerable size, has to be arranged under the user's shirt, which makes it difficult to arrange and possibly adjust the belt appropriately so as to ensure better measurement results during a physical exercise.

SUMMARY OF THE INVENTION

An object of the invention is to provide an improved method and apparatus implementing the method for measuring an electrical heart rate signal on a person's body. This is achieved by the method to be disclosed in the following. The method is a method for measuring an ECG signal on a person's skin, in which method a potential difference caused by the ECG signal is measured by means of a first electrode and a second electrode in an electrode structure that come into contact with the person's skin. In the method, the first electrode is at least partly located on an inner surface of the electrode structure to be arranged around a finger, the inner surface residing against the finger, and the second electrode is located on an outer surface of the electrode structure.

The invention further relates to an electrode structure for measuring an ECG signal on a person's skin. The electrode structure to be arranged on the person's finger comprises an inner surface residing against the finger, which inner surface of the electrode structure comprises an inner surface electrode, the electrode structure further comprising an outer surface opposite to the inner surface, which outer surface of the electrode structure comprises an outer surface electrode to be arranged against a point on the person's skin other than said finger having the electrode structure arranged thereon, the electrode structure being arranged to measure a potential difference caused by the ECG signal between a first electrode and a second electrode.

The invention further relates to a heart rate measuring arrangement for measuring an ECG signal on a person's skin. The heart rate measuring arrangement comprises an electrode structure to be arranged on the person's finger and a wrist receiver unit, which electrode structure comprises an inner surface residing against the skin on the finger, the inner surface of the electrode structure comprising an inner surface electrode, the electrode structure further comprising an outer surface opposite to the inner surface, the outer surface of the electrode structure comprising an outer surface electrode to be arranged against a point on the person's skin other than said finger having the electrode structure arranged thereon, the electrode structure comprising ECG processing means connected to the electrodes for measuring a potential difference caused by the ECG signal in a first electrode and a second electrode and for producing heart rate information on the basis of the measured potential difference, the electrode structure further comprising a transmitter for transmitting heart rate information to the wrist receiver comprising a receiver for receiving the heart rate information transmitted from the electrode structure, the wrist receiver further comprising a display for displaying the heart rate information.

Preferred embodiments of the invention are disclosed in the dependent claims.

The invention thus relates to a method and apparatus implementing the method for measuring a heart rate signal on a person's skin. The electrode structure to be used in a solution of the invention is to be arranged at least partly around the user's finger. In an embodiment, the electrode structure comprises two open ends, enabling the electrode structure to be slid over and around a considerable section of the finger. In an embodiment, the electrode structure comprises one closed end, in which case the electrode structure is slid over the finger such that the closed end resides on the fingertip. Preferably, the electrode structure is then shaped like a cylinder, i.e. it has a spherical cross-section. It is obvious that the electrode structure is not necessarily exactly cylindrical but may be e.g. conical. In a conical structure, for example the cross-section of the end of the electrode structure located farther away from the fingertip is larger than that of the end located closer to the fingertip. It is obvious that the electrode structure may also have a cross-section shaped like a square, rectangle, ellipse or the like.

On its inner surface residing against a finger, the electrode structure comprises an inner surface electrode. The electrode structure also comprises an outer surface, which is a surface with no contact with the skin on the finger having the electrode structure arranged thereon. On its outer surface, the electrode structure comprises an outer surface electrode to be arranged against a point on the person's skin other than said finger having the electrode structure arranged thereon. It is obvious to one skilled in the art that the invention is not restricted to the electrode structure only comprising one inner surface electrode and one outer surface electrode but there may be more than one such electrode. The inner surface and the outer surface of the electrode structure are electrically isolated from each other to enable a potential difference between the electrodes to be measured. In order to ensure optimal measurement of a heart rate signal, the outer surface electrode is set against a point on the skin located on a side of an electrical vector formed by the heartbeat other than the one on which said finger resides, which enables an ECG signal to be detected. During measurement, the outer surface electrode is placed e.g. against the user's forehead or finger in a hand other than the one having the electrode structure arranged thereon. In a preferred embodiment of the invention, the electrode structure comprises a control unit for determining a point in time at which the electrodes are brought into contact with the user's skin. The procedure used therein preferably employs impedance measuring or pressure measuring techniques.

Preferably, the electrodes in the electrode structure are connected to a central processing unit, which, on the basis of the heart rate signals measured by the electrodes, estimates points in time for detected heartbeats and further, on the basis of the detected points in time for heartbeats, calculates the heart rate. The central processing unit is located e.g. in a watch-like device worn on the user's wrist, such as a heart rate monitor or a wrist computer. Information is then transmitted between the electrode structure and the heart rate monitor using the known methods, e.g. optically, electromagnetically or through a transfer circuit. In such an embodiment, a display for displaying heart rate information is preferably also located in the wrist receiver. In a preferred embodiment of the invention, all necessary parts in the apparatus and procedures performed by such parts to measure, process and display heart rate information are provided and carried out in the electrode structure worn on the finger. The heart rate information is then preferably displayed by a display on the outer surface of the electrode structure, such as a liquid crystal display. It is obvious that in the case of a separate receiver unit, the display of the electrode structure and the display of the heart rate monitor are not mutually exclusive but both device units or only one such unit may comprise a display.

An advantage of the invention is that compared to the known solutions, the electrode structure is hardly noticeable and more user-friendly.

BRIEF DESCRIPTION OF THE DRAWINGS

In the following, the invention will be described in closer detail with reference to the accompanying drawings, in which FIG. 2 shows an arrangement of a preferred embodiment of the invention for producing heart rate.

DETAILED DESCRIPTION OF THE PREFERRED EMBODIMENTS

Figure 1A:
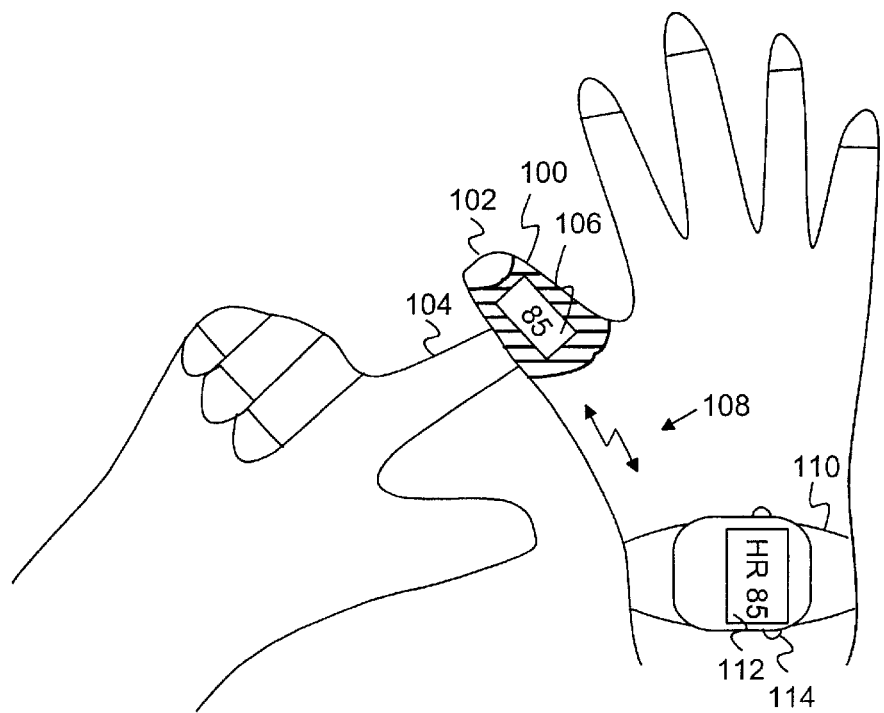
FIG. 1A shows how heart rate is measured using an electrode structure according to an embodiment of the invention.

In the following, the invention will be described by means of preferred embodiments and with reference to accompanying drawings 1A to 3. FIG. 1A shows an electrode structure 100 arranged on a person's finger 102, a thumb in the example of the figure. The disclosed electrode structure 100 is slightly conical, which means that the diameter of a cross-section of the end of the electrode structure facing the fingertip of the finger 102 is smaller than that of the end at the base of the finger 102. The disclosed electrode structure 100 has two open ends, but it is obvious that the end of the electrode structure facing the fingertip may also be a closed one, like a sheath, in which case the electrical ECG signal produced by the heartbeat can also be measured on the skin at the fingertip of the finger 102. An outer surface electrode located on the outer surface of the electrode structure 100 shown in the figure is touched e.g. by a finger 104 in the person's hand other than the one having the electrode structure arranged thereon. Preferably, using the known methods, the ECG signal to be measured is processed, i.e. filtered, amplified and detected, in the electrode structure 100 to enable heartbeats to be detected from the ECG signal to be transmitted to a receiver unit 110. For detecting the heartbeat, the electrode structure 100 measures the potential difference, or voltage, between the electrodes. The heart rate is detected e.g. on the basis of a QRS complex detectable from a heart signal, wherein the letters Q, R and S refer to potential phases in the electrical signal caused by electrical activation of the heart. In an embodiment, the QRS detection can be carried out using a matched filter, in which case a model complex is compared to the measured QRS complex in the electrode structure, and if the comparison exceeds a certain threshold limit, the measured complex is accepted as a heartbeat.

The heart rate information measured by the electrode structure 100 is delivered telemetrically 108 to the watch-like receiver unit 110 worn on the wrist, e.g. to a heart rate monitor, wrist computer or the like. The electrode structure 100 then comprises a transmitter for transmitting heart rate information to the receiver unit 110, which, in turn, comprises a receiver for receiving the information. In the case of a telemetric inductive transmission, for example, the transmitter and the receiver comprise a reel, which means that the transmission takes place as one or more magnetic pulses per each heartbeat. Instead of the transmission 108 taking place as magnetic pulses, the heart rate signal information measured by the electrodes in the electrode structure 100 can be delivered to the receiver unit 110 e.g. optically, as RF transmission, through a transfer circuit or in another such known manner.

In an embodiment, the receiver unit 110 comprises supply means 114 for giving commands to the apparatus. The commands may e.g. be commands to start/end heart rate measurement, setting heart rate limits, activating light source or other such functions in heart rate monitors. It is obvious that the necessary commands can be delivered to the electrode structure in a similar manner using the connection 108 to that described above in connection with the case of transmitting heart rate information from the electrode structure 100 to the receiver unit 110. In an embodiment, the receiver unit 100 comprises a display 112 for displaying the produced heart rate information. Heart rate information herein refers to the information produced from the heartbeat rate or information associated with physical exercise because of the heart rate, such as e.g. heart rate/minute, heart rate variance, set heart rate limits or duration of physical exercise within a certain heart rate range. In an embodiment, the electrode structure 100 comprises a display 106 for displaying heart rate information. The heart rate information to be displayed is preferably delivered to the electrode structure 100 using the same method as was used in delivering the heart rate information to the receiver unit 110, without, however, restricting the invention to such data transmission method.

Figure 1B:
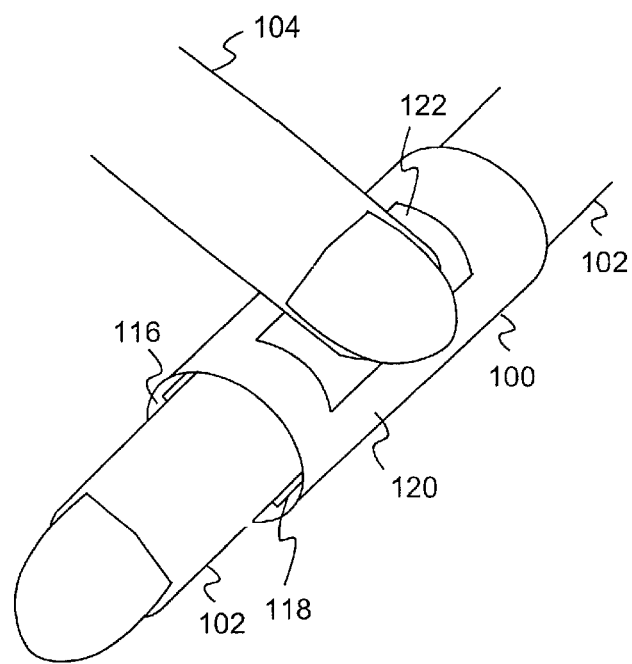
FIG. 1B shows a preferred arrangement of electrodes in the electrode structure.

FIG. 1B shows an arrangement according to a preferred embodiment of the invention. A cylindrical electrode structure 100 is arranged around a person's index finger 102. The cylindrical electrode structure 100 can be arranged on the finger 102 e.g. by pulling the finger 102 through the open end or by attaching the structure 100 to the finger 102 by means of a self-adhesive attachment strip or the like. On its inner surface 116 the electrode structure 100 comprises an inner surface electrode 118. The size of the inner surface electrode 118 is irrelevant to the invention. The finger 102 is e.g. only partly in contact with the electrode 118, which is small with respect to the inner surface, or the electrode 118 is arranged to cover the entire inner surface 116. Furthermore, on its outer surface 120 the electrode structure 100 comprises an outer surface electrode 122 to be arranged against another point on the skin. Such other point on the skin is preferably e.g. the person's forehead or the skin on the other hand. The strength of an ECG signal on the human skin mainly varies on a vector whose maximum value is obtained at the starting point of the vector at the right shoulder and the minimum point at the end point of the vector at the left heel. A maximum ECG signal can usually be measured on a human by placing the electrodes at the end points of said vector. The electrodes used in the electrode structure 100 are e.g. plastic structures corresponding to the electrodes used in the prior art heart rate monitors. The electrode structure 100 is made e.g. of isolating plastic in order to enable the electrodes 118, 122 to be electrically isolated. The electrodes 118, 122, in turn, are coated with electrically conductive material or they are made of electrically conductive plastic or metal.

Figure 1C:
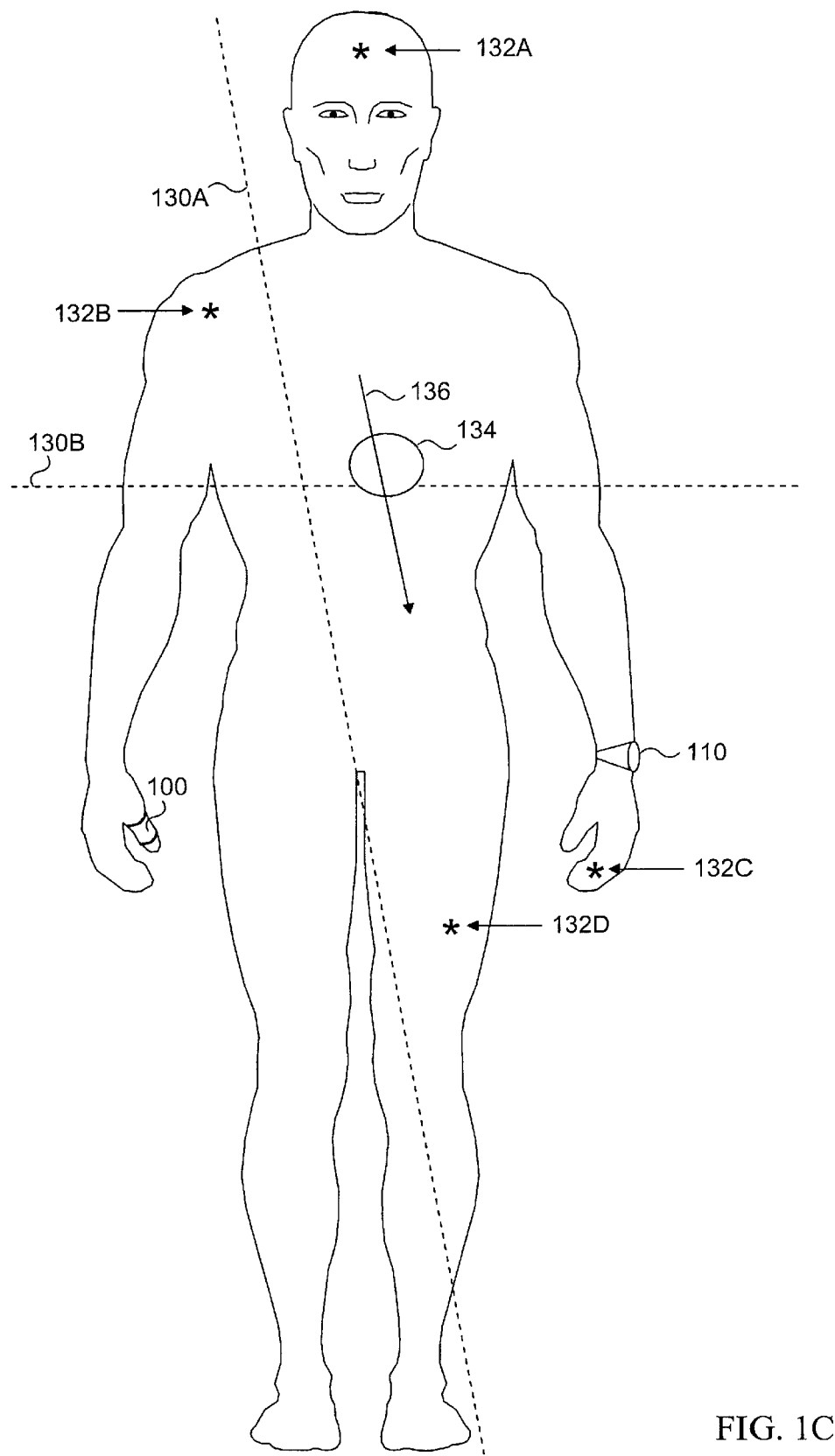
FIG. 1C shows feasible measuring points for the electrodes on a person's body.

FIG. 1C shows feasible measuring points on a person's skin regarding the way in which the electrode structure is to be positioned. In the example of FIG. 1C, the electrode structure 100 is placed on the right hand thumb while the wrist receiver 110 wirelessly receiving the heart rate information is located on the left hand wrist. In humans, the direction of an electrical activation vector 136, i.e. peak R vector of the QRS complex, produced by the beat of the heart 134 is usually slightly oblique and it is mainly located on a straight line connecting the right shoulder and the left heel. The direction of the activation vector 134 is highly individual and may, depending on the person, also be e.g. vertical or oblique, being directed from the left shoulder towards the right heel. A vertical middle line 130A and a horizontal middle line 130B can then be discerned with respect to the heart 134. The purpose of the middle lines 130A to 130B become apparent in that when in FIG. 1C the first electrode is located in a quarter located underneath the horizontal middle line 130B and on the left side of the vertical middle line 130A, the potential difference between the electrodes can be measured by placing one electrode at a point on the skin located in any one of the remaining three quarters. By way of example, the asterisks in the figure show four other points on the skin, i.e. the forehead 132A, right shoulder 132B, left hand 132C and left thigh 132D.

FIG. 2 shows the structure of the arrangement according to a preferred embodiment of the invention, wherein all structures and functions required for measuring, processing and displaying the heart rate are located in an electrode structure to be worn on the finger. The electrode structure 100, and particularly the electrodes 118, 122 therein, are used for measuring an ECG signal on the user's skin and for delivering the signal to an ECG processing unit 200. At the ECG processing unit 200, the ECG signal is subjected to necessary signal processing procedures, such as filtering and amplifying. Furthermore, at the processing unit 200, the heart rate is detected from the ECG signal by determining e.g. peak R in the QRS complex as the strongest in the signal or by detecting the timing point of the QRS complex by means of a matched filter. The produced heart rate detections are delivered to a central processing unit 202 coordinating the operation of the electrode structure 100, the heart rate detections enabling the heartbeat rate to be calculated. Other calculatory quantities, i.e. heart rate information, can be produced at a calculating unit 206 connected to the central processing unit 202 on the basis of the heartbeat rate, i.e. heart rate. Heart rate information herein thus refers e.g. to heartbeat rate, heart rate variance, rate of change in heart rate, heart rate limit or other such quantity. The electrode structure 100 operating as a heart rate monitor further comprises supply means 114 for providing input data, i.e. for detecting when measuring the heart rate starts and ends. The supply means 114 can be implemented e.g. as push buttons, contact area on a display, speech control or the like. The electrode structure 100 further comprises a memory 204 containing a short-term RAM memory for storing the heart rate information or the like, and a ROM memory for storing necessary programs.

The electrode structure 100 preferably comprises a control unit 210 connected to the central processing unit 202 to enable points in time at which ECG signal measurement is to be started and ended to be controlled in the electrode structure 100. The point in time at which ECG signal measurement is to be started can be determined e.g. by conveying an extremely low current, e.g. 50 nanoamperes, through a pair of electrodes, and measuring the voltage between the measuring electrodes. The measured voltage divided by the current used gives the impedance between the measurement electrodes. The impedance indicates whether a measurement procedure is to be started, i.e. whether the electrodes 118, 122 are connected to their measuring points. For example, if the impedance between the electrodes 118, 122 is less than one megaohm, the measurement will be started. The point in time at which the measurement is to be started can also be determined using pressure-sensitive PVDF films to indicate when the upper surface of the electrode structure has been pressed hard enough against the lower surface so as to start the measurement. In a preferred embodiment, a device 208 for delivering sound signals in the electrode structure 100 gives a sound signal each time the measurement starts successfully. Signals are measured e.g. for 10 seconds, after which the device 208 for delivering a sound signal preferably gives a second sound signal in order to indicate that the measurement has been completed. The measurement result is then displayed on a display 112 either until the next measurement or e.g. for 15 seconds. The display 112 is implemented e.g. as a liquid crystal display and, in addition to the heart rate, the information displayed on the display includes e.g. heart rate parameters deducible from the heart rate or numerical values relating to physical exercise, such as heart rate limits, duration of exercise or the like. The control unit 210 thus comprises means for measuring impedance between the electrodes, means for inferring, on the basis of the measured impedance, whether the electrodes come into contact with the user's skin, and means for monitoring the ECG signal measurement time.

The necessary devices in the different parts of the arrangement, such as the central processing unit 202, the calculating unit 206 and the control unit, are preferably implemented by software using a general-purpose microprocessor; however, different hardware implementations, e.g. a circuit built using separate logic components or one or more ASICs (Application Specific Integrated Circuit), are also feasible.

Figure 3:
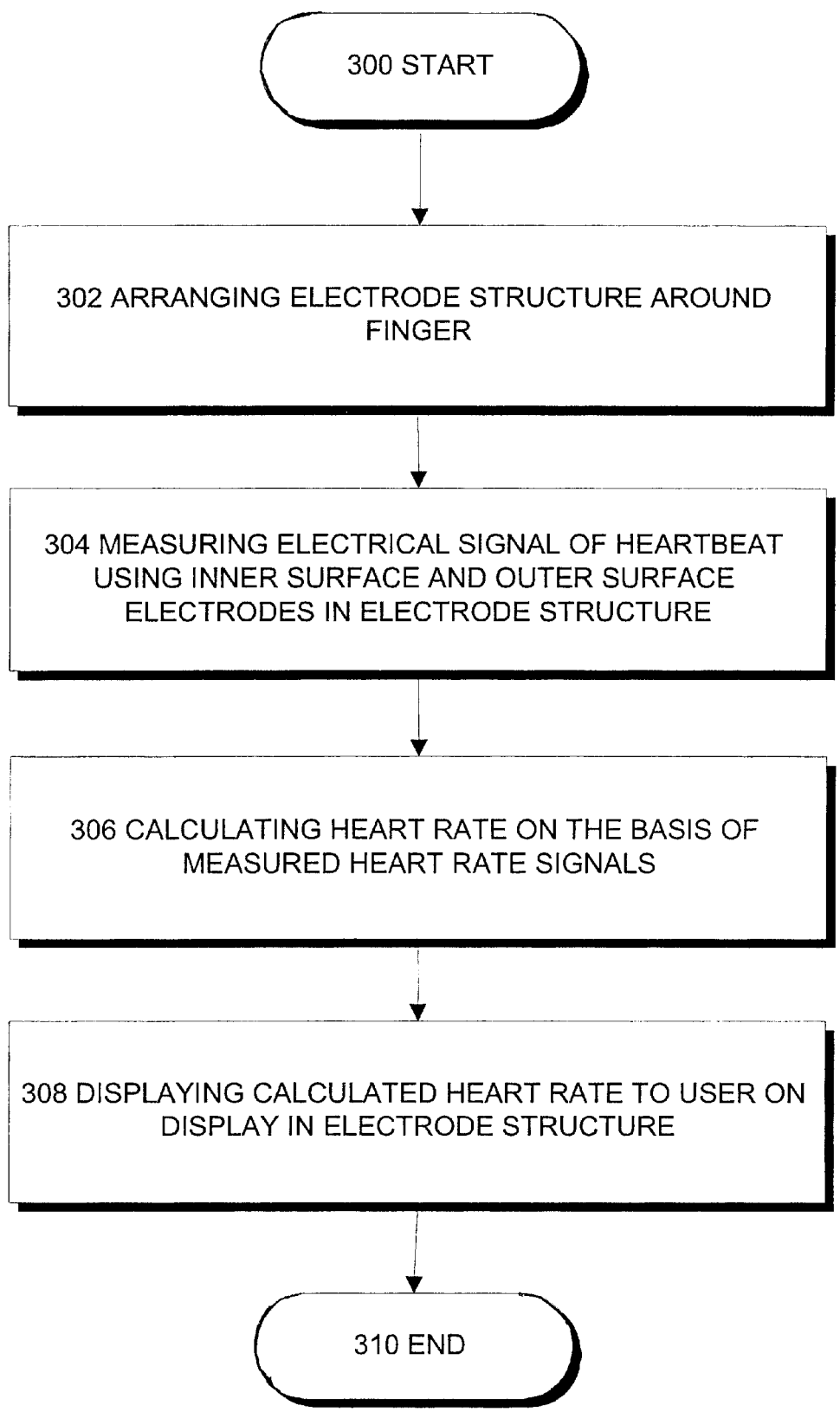
FIG. 3 shows a preferred embodiment of a method according to the invention.

Referring to FIG. 3, a preferred embodiment of a method according to the invention will be described. In starting step 300 of the method, a user is preparing e.g. for a physical exercise, planning to measure his or her heart rate during the exercise. In step 302, an electrode structure according to the invention is arranged e.g. around the left hand thumb. It is obvious that to ensure that the electrode structure fits the finger appropriately, the structure may be provided with tightening means, e.g. self-adhesive or belt tightening means. Furthermore, the electrode structure can be made of flexible material and it can have a small cross-section so as to enable the structure to tighten in its place around a finger.

In method step 304, an electrical ECG signal produced by the heartbeat is measured in connection with physical exercise, using an inner surface electrode located on the inner surface of the electrode structure and an outer surface electrode located on the outer surface thereof. During measurement, the inner surface electrode resides against said left hand thumb while the outer surface electrode can be positioned e.g. against a right hand finger, right hand wrist, right thigh or other such point on the skin residing in a different quarter shown in FIG. 1C. In a preferred embodiment of the invention, the electrode structure comprises a display. On its outer surface, preferably on its opposite sides, the electrode structure then comprises a display and an electrode, without, however, restricting the invention to the way in which these two are positioned with respect to each other; the display and the outer surface electrode may also be located on the same side of the electrode structure. The electrodes, in turn, are with respect to each other preferably positioned such that when the outer surface electrode is located on the lower surface of the outer surface, i.e. on the opposite side of a nail, the inner surface electrode is located on the lower surface of the inner surface, residing against the lower surface of the finger when in use. The inner surface electrode and the outer surface electrode are then oppositely located on different sides of the lower surface of the electrode structure, and if the outer surface electrode is pressed against another point on the skin, the inner surface electrode will also be pressed against the inner surface of the finger so as to provide a more accurate measurement result.

In method step 306, the heart rate is calculated on the basis of the measured heart rate signals. Depending on the embodiment of the solution in accordance with the invention, the heart rate is calculated using the calculating means in the electrode structure or the measured heart rate information is transmitted to a separate receiver unit, e.g. to an apparatus worn on the wrist, for further processing. In method step 308, the heart rate information is displayed to the user on the display of the wrist receiver and/or the electrode structure, on the basis of which information the user is able to adjust his or her training intensity as desired.

Although the invention has been described above with reference to the examples in the accompanying drawings, it is obvious that the invention is not restricted thereto but can be modified in many ways within the scope of the inventive idea disclosed in the attached claims.

What is claimed is:

1. An electrode structure for measuring an EGG signal on a person's skin, wherein the electrode structure is adapted to be arranged and substantially retained at least partly around the person's finger comprises an inner surface adapted to reside against the finger, which inner surface of the electrode structure comprises a first electrode, the electrode structure further comprising an outer surface opposite to the inner surface, which outer surface of the electrode structure comprises a second electrode adapted to be arranged against a point on the person's skin other than said finger having the electrode structure arranged thereon, the electrode structure being arranged to measure a potential difference caused by the EGG signal between said first electrode and said second electrode.

2. An electrode structure as claimed in claim 1, wherein the second electrode is adapted to be arranged against the skin on the person's hand other than the hand having the electrode structure arranged at least partly around its finger for measuring the potential difference caused by the ECG signal between the electrodes.

3. An electrode structure as claimed in claim 1, wherein the electrode structure is cylindrically shaped in order to ensure a contact between the first electrode and the skin on the finger.

4. An electrode structure as claimed in claim 1, wherein the electrode structure is a cylindrical structure comprising two open ends in order to enable the electrode structure to be arranged around the finger.

5. An electrode structure as claimed in claim 1, wherein the electrode structure comprises a central processing unit connected to the electrodes for producing heart rate information on the basis of the ECG signal measured by the electrodes.

6. An electrode structure as claimed in claim 1, wherein on its outer surface the electrode structure comprises a display for displaying heart rate information.

7. An electrode structure as claimed in claim 1, wherein the electrode structure comprises a control unit for monitoring a point in time at which the electrodes in the electrode structure are brought into contact with the person's skin.

8. An electrode structure as claimed in claim 7, wherein the electrode structure is arranged to start measuring the ECG signal on the basis of the point in time detected by the control unit at which the electrodes are brought into contact with the skin.

9. An electrode structure as claimed in claim 7, wherein the control unit, while monitoring the point in time at which skin contact occurs, is arranged to feed electric current to the electrodes, monitor impedance of a circuit formed by the electrodes, and when the impedance drops below a threshold value, to infer that the electrodes have been brought into contact with the skin.

10. An electrode structure as claimed in claim 7, wherein the electrode structure comprises a pressure-sensitive film in connection with the electrodes for detecting skin contact of the electrodes.

11. A heart rate measuring arrangement for measuring an ECG signal on a person's skin, wherein the heart rate measuring arrangement comprises an electrode structure adapted to be arranged on the person's finger and a wrist receiver unit, which electrode structure comprises an inner surface adapted to reside against the skin on the finger, the inner surface of the electrode structure comprising a first electrode, the electrode structure further comprising an outer surface opposite to the inner surface, the outer surface of the electrode structure comprising a second electrode adapted to be arranged against a point on the person's skin other than said finger having the electrode structure arranged thereon, the electrode structure comprising ECG processing means connected to the electrodes for measuring a potential difference caused by the ECG signal in said first electrode and said second electrode and for producing heart rate information on the basis of the measured potential difference, the electrode structure further comprising a transmitter for transmitting heart rate information to the wrist receiver comprising a receiver for receiving the heart rate information transmitted from the electrode structure, the wrist receiver further comprising a display for displaying the heart rate information.

12. A heart rate measuring arrangement as claimed in claim 11, wherein the second electrode is adapted to be arranged against the skin on the person's hand other than the hand having the electrode structure arranged on its finger for measuring the potential difference caused by the ECG signal between the electrodes.

13. A heart rate measuring arrangement as claimed in claim 12, wherein the inner surface and the outer surface of the electrode structure are made of electrically isolating material in order to enable the inner surface electrode and the outer surface electrode to be electrically isolated from each other.

14. A heart rate measuring arrangement as claimed in claim 12, wherein the electrode structure is cylindrically shaped in order to ensure a contact between the first electrode and the skin on the finger.

15. A heart rate measuring arrangement as claimed in claim 11, wherein the electrode structure comprises a control unit for monitoring a point in time at which the electrodes in the electrode structure are brought into contact with the person's skin.

16. A heart rate measuring arrangement as claimed in claim 15, wherein the heart rate measuring arrangement is arranged to start measuring the ECG signal on the basis of the point in time detected by the control unit at which the electrodes are brought into contact with the skin.

17. A heart rate measuring arrangement as claimed in claim 15, wherein the control unit, while monitoring the point in time at which skin contact occurs, is arranged to feed electric current to the electrodes, monitor impedance of a circuit formed by the electrodes, and when the impedance drops below a threshold value, to infer that the electrodes have been brought into contact with the skin.

18. A heart rate measuring arrangement as claimed in claim 15, wherein the electrode structure comprises a pressure-sensitive film in connection with the electrodes for detecting skin contact of the electrodes.

* * * * *

UNITED STATES PATENT AND TRADEMARK OFFICE
CERTIFICATE OF CORRECTION

PATENT NO. : 6,754,517 B2
DATED : June 22, 2004
INVENTOR(S) : Seppo Nissilä

It is certified that error appears in the above-identified patent and that said Letters Patent is hereby corrected as shown below:

Column 7,
Line 63, now reads "Measuring an EGG signal on", and should read -- Measuring an ECG signal on --.

Column 8,
Line 8, now reads "the EGG signal between", and should read -- the ECG signal between --.

Signed and Sealed this

Fourteenth Day of September, 2004

JON W. DUDAS
*Director of the United States Patent and Trademark Office*